United States Patent [19]

Göbel et al.

[11] Patent Number: 4,562,585
[45] Date of Patent: Dec. 31, 1985

[54] SEQUENTIAL X-RAY CRYSTAL SPECTROMETER

[75] Inventors: Herbert Göbel; Rupert Köpl, both of Munich, Fed. Rep. of Germany

[73] Assignee: Siemens Aktiengesellschaft, Berlin & Munich, Fed. Rep. of Germany

[21] Appl. No.: 724,953

[22] Filed: Apr. 22, 1985

Related U.S. Application Data

[63] Continuation of Ser. No. 390,993, Jun. 22, 1982.

[30] Foreign Application Priority Data

Jun. 30, 1981 [DE] Fed. Rep. of Germany ....... 3125803

[51] Int. Cl.$^4$ .............................................. G01T 1/36
[52] U.S. Cl. ........................................ 378/83; 378/49
[58] Field of Search ........................ 378/82, 83, 84, 49

[56] References Cited

U.S. PATENT DOCUMENTS

| | | | |
|---|---|---|---|
| 3,663,812 | 5/1972 | Koenig | 378/83 |
| 4,131,794 | 12/1978 | Bruninx | 378/83 |
| 4,144,450 | 3/1979 | Göbel | 250/272 |

OTHER PUBLICATIONS

Siemens, "Röntgen-Analysengeräte", Catalog MP 42, 1980.
Siemens-Werbebroschüre MRS 400, No. E6892/1007, "Multichannel X-ray Spectrometer".
E. Bruninx, Philips Research Reports, "A Study of Different Geometries for the Seemann X-ray Spectrometer Equipped with a Position-Sensitive Detector", vol. 32, No. 4, (1977), pp. 253-265.
E. Bruninx, Spektrochimica Acta, "X-ray Fluorescence Analysis by Means of Crystal Dispersion and a Position-Sensitive Counter", vol. 31B, (1976), pp. 221-223.

*Primary Examiner*—Craig E. Church
*Attorney, Agent, or Firm*—Hill, Van Santen, Steadman & Simpson

[57] ABSTRACT

A sequential x-ray spectrometer has a curved analyzer crystal and a position-sensitive detector. In order to obtain a high quantum yield or efficiency, an extensive suppression of scattered background radiation, and an increase of the measuring speed, the position-sensitive detector is arranged in a mobile fashion.

19 Claims, 11 Drawing Figures

SEQUENTIAL X-RAY CRYSTAL SPECTROMETER

This is a continuation of application Ser. No. 390,993, filed June 22, 1982.

BACKGROUND OF THE INVENTION

The invention relates to a sequential x-ray crystal spectrometer for analyzing x-ray radiation from a sample wherein a curved analyzer crystal and a position-sensitive detector is provided for measuring x-ray radiation intensity.

Sequential x-ray crystal spectrometers for conventional construction are described e.g. in "Analytical X-Ray Systems Catalog, Siemens MP 42 (1980)", incorporated herein by reference. Essentially the fluorescent radiation emanating from a large-surface sample is brought to diffraction on a planar analyzer crystal, and the radiation intensity detected on a large-surface detector is measured as a function of the position (angle $\theta$) of the analyzer crystal. The resolution of such a system is determined by the acceptance angle (e.g. 0.1°) of a Soller collimator between sample and analyzer crystal. The geometric efficiency of the measurement results as the product of sample surface and solid angle, that is as the product of a large surface and a very small solid angle. The detector is here given only the role of recording the diffracted x-ray quanta. Information concerning at which location of the detector surface the diffracted x-ray quanta strike is without significance herein.

Also known is a multi-channel spectrometer (Siemens Advertising Brochure MRS400, Order No. E6892/1007), incorporated herein by reference, in which the principle of the "Seemann-Bohlin focusing geometrie" is employed. In the case of such a multi-channel spectrometer, for each element to be analyzed, a permanently set curved analyzer crystal is employed which, together with diaphragms and a respective detector, defines one channel each. Since no parts need be moved, the ray or beam path is here readily evacuatable so that elements can be detected up to a very low atomic number (carbon). Entry and exit slits precisely define the ray trace so that the background can be kept very low. The x-ray output can here be indicated proportionally to the product of the entry slit and beam divergence, i.e. a small surface and a large solid angle. In the case of a multi-channel spectrometer, the x-ray output should have approximately the same order of magnitude as in the case of conventional sequence x-ray spectrometers.

An elegant solution for the sequential detection of a wide spectral range is the focusing linear spectrometer, such as has been realized in the so-called "scanner" of the multichannel spectrum "Siemens MRS400" system, incorporated herein by reference. Measurement can here be carried out with a fixed detector voltage and a fixed discriminator window, as a consequence of which higher orders of diffraction as well as uncorrelated stray radiation can be eliminated.

With a position-sensitive resolution detector (PSD), it is possible to detect simultaneously several elements in a focusing arrangement. A x-ray spectrometer with a PSD and a focusing analyzer crystal thus functions in a restricted wavelength range like a multi-channel spectrometer. The diffraction $2\theta$ can be read off linearly on the focusing circle. A position-sensitive proportional counter (PSPC), however, permits no oblique beam incidence, so that its window must always be aligned perpendicularly to the crystal center. This inevitably leads to a violation of the focusing conditions and to a distortion of the location scale along the counter wire, whereby the distortion is proportional to the distance of detector/crystal center. In the case of a x-ray spectrometer with a PSPC with a focusing analzyer crystal, favorable conditions result for a precise measurement only in a restricted angular range about the detector center. In addition, there is the fact that different wavelengths are detected from different locations on the sample.

E. Bruninx (Philips' Research Reports 32 (1977) 253265 and Spektrochimica Acta 31B, (1976) Page 221, incorporated herein by reference) showed experiments with different geometric arrangements in the case of such a x-ray spectrometer with a PSPC and a focusing crystal, whereby a stationary PSD could resolve without difficulties, adjacent elements in the wavelength range of about 0.15 nm (CuK$\alpha$). However, in comparison with the results thus achieved, an energy-dispersive spectrometer shows an improved performance which, although exhibiting a poorer resolution, delivers instead a more favorable peak-background ratio and substantially higher yields or efficiency.

SUMMARY OF THE INVENTION

An object of the invention is to provide a sequential x-ray crystal-spectrometer of the initially cited type which permits a high yield or output, an extensive suppression of background radiation, and an increase of the measuring speed in crystal x-ray spectrometers.

In accordance with the invention, this object is achieved by a spectrometer having a curved analyzer crystal, means for moving the analyzer crystal, and position-sensitive detector means for measuring x-ray radiation intensity, wherein means are provided for moving the position-sensitive resolution detector means during analysis.

The principle of the moving PSD permits a relatively narrow definition of the beam path. However, this beam path can nevertheless be selected orders of magnitude broader than in the case of the above-cited "scanner", so that the defocusing remains low and an extensive reduction of the background is possible. The rotation of the analyzer crystal leads to a successive scanning of the entire sample surface.

In utilizing a focusing (Johannsson-) analyzer crystal, the fluorescent radiation detected for the analysis is imaged on a focusing circle (Seeman-Bohlin-Geometrie). As a position-sensitive detector, a position-sensitive resolving solid state detector or also a locally resolving proportional counter tube can be employed. The principle of the continuously moved PSD is particularly favorable (See CPSD: H. E. Göbel in "Advances in X-Ray Analysis 22, (1979) 255–265, incorporated herein by reference).

If both the detector as well as the analyzer crystal are rotated, and if the rotation of the detector is twice as much as the rotation of the analyzer crystal ($\theta$-$2\theta$-rotation) and wherein a simultaneous displacement of the detector on the focusing circle guarantees that the center of the detector remains in the focus, it is possible to scan the entire angular range $2\theta$ from approximately 20° to 140°, and to thus detect a broad wavelength range.

On account of the focusing property of the analyzer crystal, a substantially larger solid angle of the emitted fluorescent radiation is analyzed and the sample surface is sequentially scanned through the rotation of the crystal. In utilizing the CPSD principle, equal wavelengths are summed up into the same channels, as a consequence of which, in comparison with a conventional crystal x-ray sequence spectrometer, approximately 10 to 100 times higher yields or outputs are obtained. The invention is clearly illustrated in the drawing and shall be explained in more detail in the following:

DESCRIPTION OF THE PREFERRED EMBODIMENTS

Figure 1:
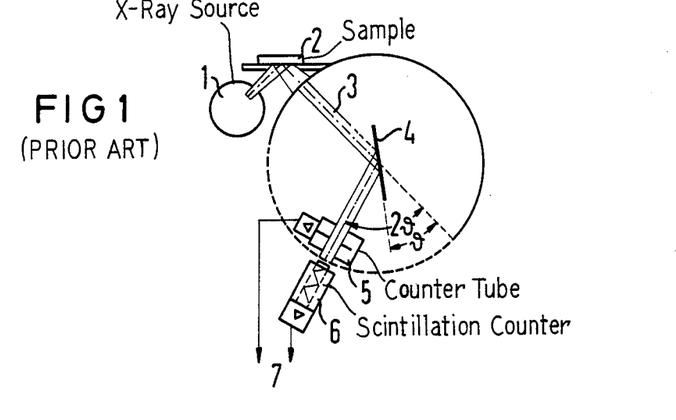
FIG. 1 represents the measuring principle of a conventional sequence x-ray spectrometer.

FIG. 1 illustrates the measurement principle of a conventional sequencial x-ray spectrometer. Such a conventional sequencial x-ray spectrometer is, e.g., described as sequencial x-ray spectrometer SRS 200 in "Analytical X-Ray Systems" Siemens Catalog MP 42 (1980), incorporated herein by reference. From a x-ray source 1, x-rays strike a sample 2. A radiation beam defined or condensed in virtually parallel fashion by means of a collimator 3 strikes an analyzer crystal 4, and is dispersed or split into a spectrum through diffraction on the lattice planes disposed parallel to the surface. The Bragg equation applies:

$$n \cdot \lambda 2d \cdot sine\ \theta,$$

with n=order of the interference, $\lambda$=wavelength, d=lattice plane interval and $\theta$=Bragg refraction angle.

If the analyzer crystal 4 is rotated in this radiation beam, then successively different wavelengths come into diffraction condition reach diffraction so that a histogram of the intensity as a function of $\theta$ reproduces the fluoescent x-ray spectrum emitted by the sample 2. The gas flow counter tube 5 and the scintillation counter 6, together with the electronic measuring apparatus, provide the possibility of a coarse energy selection of the recorded quanta. It is thereby possible to measure with a desired interference order n and to reduce the influence of scattered background radiation to a minimum. From the Bragg equation, it is apparent that the quantum energies, which are proportional to $1/\lambda$, are conversely proportional to sine $\theta$. The pulse heights of the radiation recorded in the detector arrangement are therefore intensified or amplified proportionally to sine $\theta$ ("Sine amplifier"). Thus, it is possible to measure with a fixed detector voltage and discriminator adjustment.

Figure 2:
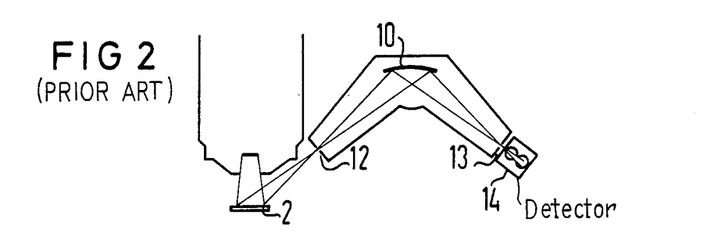
FIG. 2 shows the ray trace in a known multi-channel spectrometer.

FIG. 2 illustrates the beam path in a known multi-channel spectrometer. Since a curved analyzer crystal 10 in a focusing arrangement is employed, the collimator of FIG. 1 can be replaced by diaphragms 12, 13. The fluorescent x-ray spectrum emitted by the sample 2, subsequent to diffraction on the analyzer crystal 10, is recorded in the detector 14.

Figure 3:
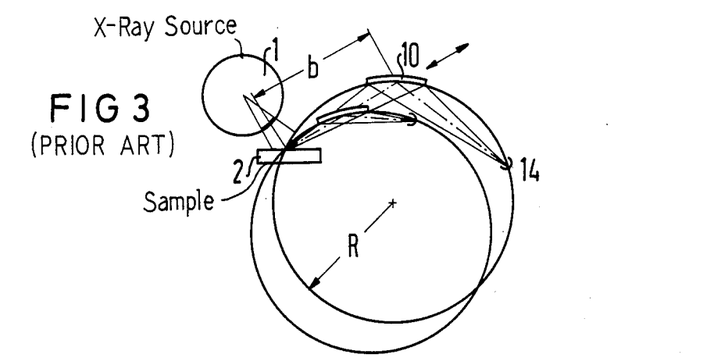
FIG. 3 shows the known method of operation of the "scanner"

FIG. 3 shows the known method of operation of the "scanner". The x-ray light emanating from the x-ray tube 1 strikes the sample 2. The fluorescent x-ray spectrum emitted by the sample 2 is diffracted on the analyzer crystal 10 and recorded by the detector 14. With a focusing linear-spectrometer, such as is realized in the "scanner" to the multichannel spectrometer "Siemens MRS 400", an additional spectral range can be sequentially detected. With a "scanner" according to FIG. 3, an angular range of $30° \leq 2\theta \leq 120°$ can be dectected. This linear spectrometer obtained its name because a linear relation exists between the wavelength $\lambda$, and a rectilinear displacement b (with simultaneous rotation) of the analyzer crystal 10. Analyzer crystal 10 and detector 14 are moved such that, with coupled $\theta 2\theta$-rotation, sample 2 and detector 14 (or entry and exit diaphragm, respectively) always remain in focus.

The interval of the sample 2 to the analzyer crystal 10 is b, with $$b = 2R \cdot sine\ \theta,$$

whereby R is the radius of the focusing circle. If one eliminate sine $\theta$ from the equation with the aid of the Bragg equation, one thus obtains $$n \cdot \lambda = (d/R) \cdot b.$$

The wavelength $\lambda$ is thus proportional to b. The interval b of the sample 2 relative to the analyzer crystal 10 is a linear scale for the wavelength $\lambda$. For this reason the "scanner" possesses a stepping motor drive which linearly alters the length b. As is apparent from FIG. 3, the analyzer crystal 10 in each position detects the same solid angle from the sample 2.

The detector pulses are so intensified that, independently of the quantum energy E, equal pulse heights result; i.e., on account of $$E \sim 1/\lambda \sim 1/b$$

the detector pulses are modulated with a factor proportional to b ("1/b-amplifier"). Thus, it is possible to measure with a fixed detector voltage and a fixed discriminator window. Accordingly, higher orders of diffraction as well as uncorrelated background radiation can be eliminated.

Figure 4:
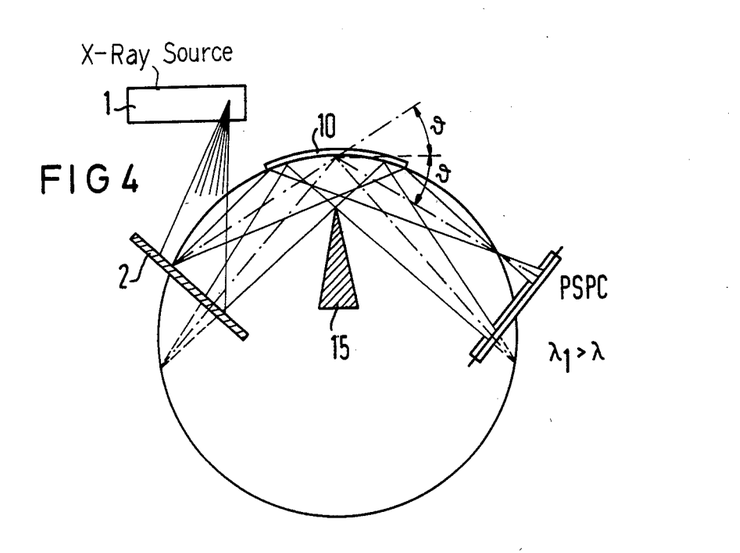
FIG. 4 shows the simultaneous detection of two wavelengths with a PSPC.

FIG. 4 illustrates the simultaneous detection of two wavelengths with a locally resolving detector (PSD). With a locally resolving detector (PSD) it is possible to simultaneously detect several elements in a focusing arrangement. An x-ray spectrometer with a locally resolving detector (PSD) thus operates in a limited wavelength range like a multi-channel spectrometer. The x-ray light emanating from the x-ray source 1 strikes the sample 2. The fluorescent x-ray spectrum diffracted on the Johannsson analyzer crystal 10 strikes a PSPC. The diffraction angle 2 can basically be linearly read off on the focusing circle. The PSPC, however, permits no oblique ray incidence, so that its window must always be aligned perpendicularly to the center of the analyzer crystal 10. This inevitably leads to a violation of the focusing conditions and to a distortion of the local scale along the counting wire proportional to the distance of the PSPC and the center of the crystal 10. Favorable conditions result only in a restricted angular range about the center of the PSPC. Also, different wavelengths from different locations on the sample 2 are detected. The knife edge diaphragm 15 serves the purpose of suppression of the background.

Figure 5:
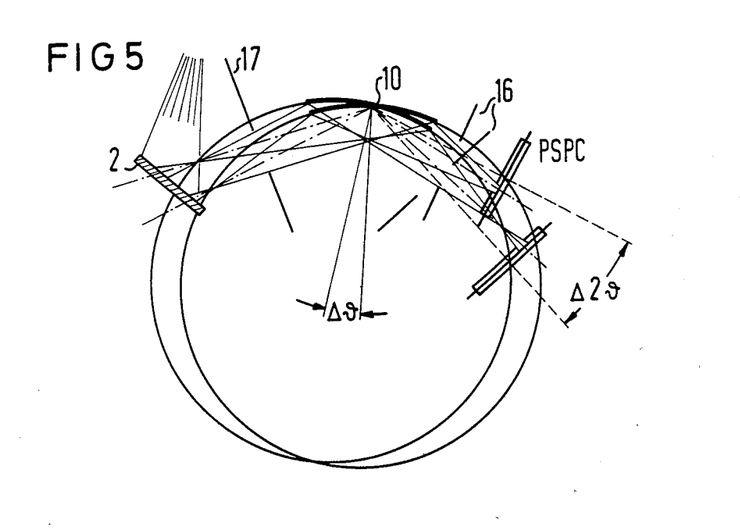
FIG. 5 shows an inventively coupled $\theta$-$2\theta$-movement of the analyzer crystal and detector, and wherein the beam path for a specific wavelength is shown.

FIG. 5 shows an inventively coupled $\theta$-$2\theta$ movement of analyzer crystal 10 and PSPC. The principle of the continuously moved PSD is employed which is designated as the CPSD principle (H. E. Göbel: Advances in X-ray Analysis 22 (1979), 255–265, incorporated herein by reference). This CPSD principle permits a relatively narrow localization or bounding of the detected radiation beam, which nevertheless can be selected orders of magntitude broader than in the case of the "scanner", so that the defocusing remains minimal and an extensive reduction of the background is possible. The rotation of the analyzer crystal 10 leads to a successive scanning of the entire surface of the sample 2. FIG. 5 illustrates the beam path for a constant wavelength with two different positions of the crystal 10. The PSPC was here rotated through double the angle ($\theta$-$2\theta$-movement) and was simultaneously so displaced on the focusing circle that the center of the detector PSPC remains in the focus.

In order that both radiation beams of equal wavelength, diffracted on the analyzer crystal 10, are counted into the same channels, the CPSD principle in a modified form must be applied: the channel address for the diffraction angle 2 of an x-ray quantum results, as in the case of the cited work of H. E. Göbel, through addition of the addresses for the angular position of the PSD and the incidence location of the quantum in the PSD. These two quantities, namely the address for the angular position of the PSD and the incidence location of the quantum in the PSD, must be digitized in linear fashion and in the same scale; i.e., in units of angle of $2\theta$. As is apparent from FIG. 5, the distance of the crystal 10 relative to the detector PSPC varies during rotation, so that the angular scale for the incidence location in the PSPC no longer remains constant. It must be divicded through this distance. If instead of a PSPC (2), a position-sensitive solid state detector is employed, this solid state detector can be tangentially guided along the focusing circle. In utilizing such a position-sensitive solid state detector, the diffraction angle 2 theta could be directly linearly read off on the focusing circle.

If one considers the geometric yield or efficiency of an inventive method according to FIG. 5, a value results which is proportional to the sample surface by the entry window 17 multiplied by the solid angle detected by the crystal 10. A method according to FIG. 5 thus relates the advantages of a focusing method, such as in the case of the "scanner" of the multi-channel spectrometer MRS 400, and the large-surface analysis, such as in the case of a conventional sequence x-ray spectrometer. Accordingly, the system of the invention is more rapid than prior known systems. Basically an increase of the measuring speed is conceivable which lies on the same order of magnitude as in the case of the CPSD diffraction methods in the cited work of H. E. Göbel; i.e., a factor of 10 to 100.

Figure 6:
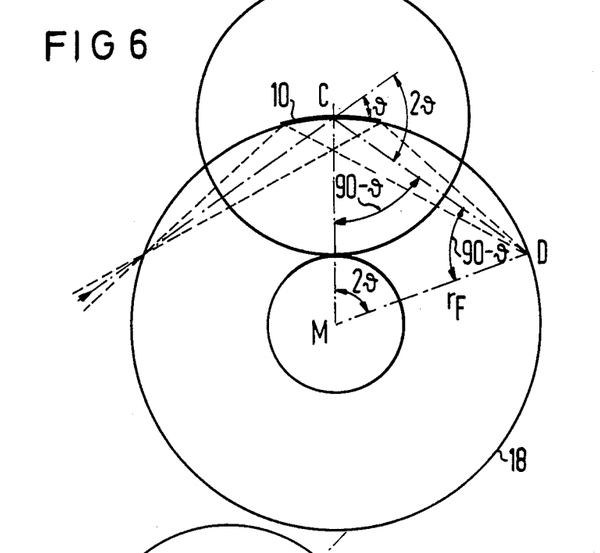
FIG. 6 illustrates geometric considerations relating to the inventively coupled $\theta$-$2\theta$-movement.

FIG. 6 represents geometrical considerations regarding the coupled $\theta$-$2\theta$-movement. In the construction of an inventive spectrometer the drive $\theta$ (or $2\theta$), respectively, is linearly selected in order to guarantee as simple as possible an application of the CPSD fundamental concept. Thus, one can either place a stepping motor drive on the rotational axis C of the crystal 10 or in the center M of the focusing circle 18. A coupling of $\theta$ and $2\theta$ is mechanically executed by means of the unwinding movement of a circle about M with the radius $r_F/3$ on a stationary circle around C with the radius $2/3 \cdot r_F$, where C is the $\theta$-rotational axis. The detector D then always sees the crystal center C at the angle $2\theta$ relative to the primary ray direction. An electronic coupling via two stepping motor drives with the rotational axes C and M is also equally possible.

Figure 7:
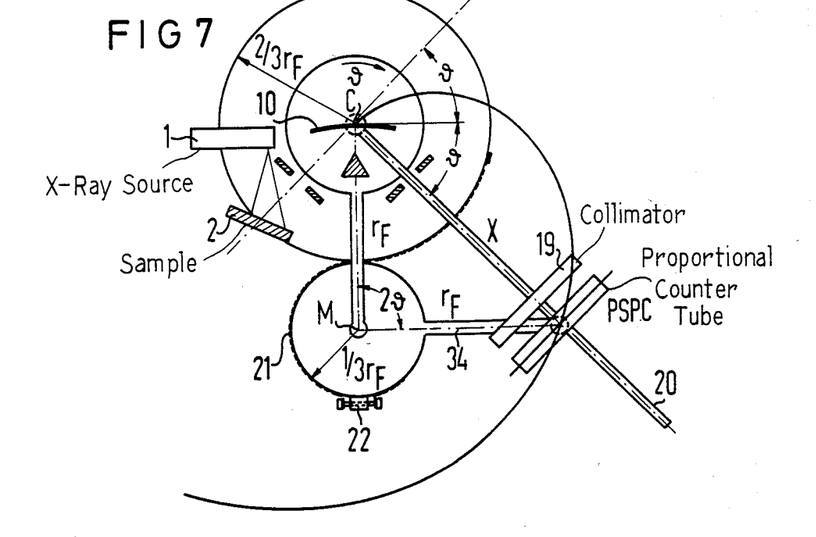
FIG. 7 shows a diagram of the coupled $\theta$-$2\theta$-movement in the case of Seemann-Bohlin focusing.

FIG. 7 shows the diagram of the coupled $\theta$-$2\theta$-movement in the case of Seemann-Bohlin focusing. The mechanical coupling of $\theta$ and $2\theta$ is here employed, whereby the drive for the rotation is placed on the adjacent rotation axis C of the crystal 10. As a drive for the rotation a play-free single circle goniometer (Huber 410), a 5-phase stepping motor (Berger RDM 564/50) with 1000 steps per degree is employed. For actuation of the drive there is a computer-linkable supply unit (laser optronics SMC 500).

In order to realize a uniform and, above all, play and backlash free rolling movement of the $2\theta$ cylinder with the center M on the fixed goniometer circle with the center C, two steel bands 21 are placed in S-shape around the two cylinder surfaces. The spring steel bands wind themselves up and unwind themselves in opposite directions in each case.

One of the two spring steel bands 21 is illustrated in FIG. 7 as a dotted line. The precise $\theta$-$2\theta$-adjustment, as well as the tensioning of the spring steel band 21, proceed on the basis of the indicated adjusting or set screws 22. With the combined $\theta$-$2\theta$-movement, the center of the PSPC describes a spiral-shaped curve.

In FIG. 7 a guide arm 20 is indicated which is rotatably mounted about the crystal center C. On the latter, a guide carrying the PSPC and a collimator 19 rolls, which is rotatably connected to the $2\theta$-arm 34. The PSPC-wire is always perpendicularly aligned to the crystal center C, so that the diffracted x-rays always fall virtually perpendicularly into the detector.

As discussed in connection with FIG. 5, the distance x between counter wire center and crystal center C must be taken into consideration when digitizing of the incidence location of an x-ray quantum in the PSPC. This is accomplished since x is converted into an electric signal which the local information is divided. The simplest solution for this is offered by a linear encoder (Messring Company, Munich 40, Type TU 150-K-1), which operates according to the principle of an inductive differential choke with an ac current bridge circuitry (carrier frequency 5 kHz). The cores of the series TU can be supplied in lengths of 150 mm to 2000 mm and have a measuring accuracy of 0.5%.

Figure 8:
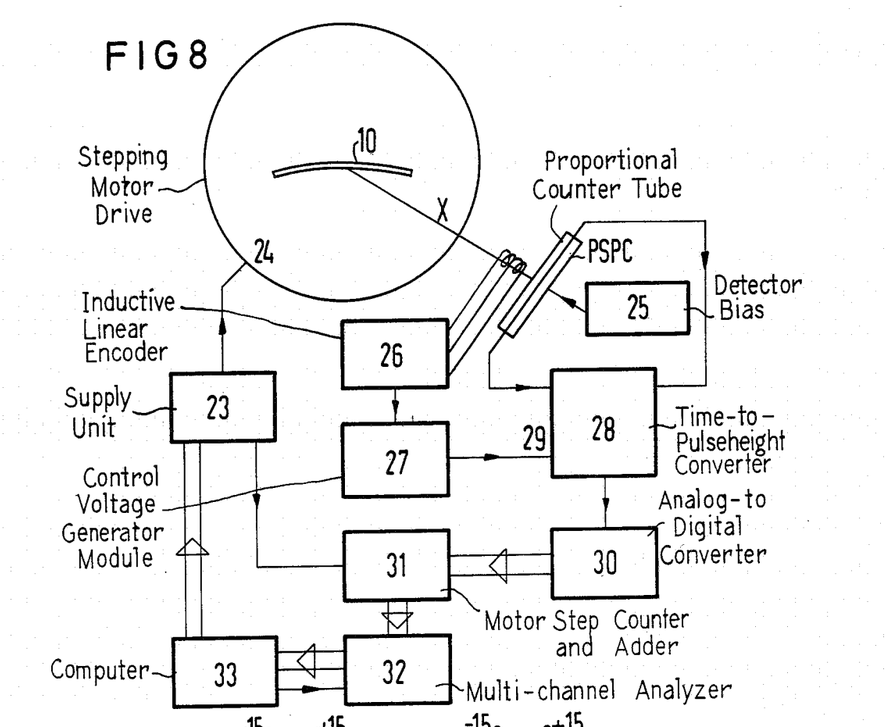
FIG. 8 shows a block diagram for the electronic circuit of an embodiment of the invention.

FIG. 8 illustrates a block diagram of the electronic construction of an inventive spectrometer. The arrangement fully corresponds to the CPSD-fundamental idea such as is disclosed in the cited work of H. E. Göbel, however with the addition of a continuously variable scale for the local information (incidence location in the PSPC) through an external voltage control. Coupled to a computer 33 is supply unit 23 which activates the stepping motor drive 24. The detector voltage is regulated via 25. The distance x between counting wire center and crystal center C is converted with the aid of a path-measured value pickup into an electric signal. Since the time-digital-converter (TDC) employed in the cited work of H. E. Göbel permits too low a dynamic range (factor 2), the originally slower path of the digitizing via a combination time-amplitude converter (TPC) 28/analog-to-digital converter (ADC) 30 is followed. For this purpose, a modified compact PSPC amplifier module is employed. The output amplifier of the TPC is so designed that the amplitudes are amplified proportionally to an externally applied control voltage (input 29). The control voltage can lie between 0 and 10 volts, whereby frequencies in the kHz range are permissible. In the instant care, the control voltage is a slowly variable dc voltage. The control voltage is generated in the module 27 which is described in greater detail in FIG. 9. In the motor step counter and adder 31, the data from the stepping motor control 23 and from the analog-to-digital converter ADC 30 are received, added and transmitted to the multi-channel analyzer 32 from which the computer 33 can finally recall them.

Figure 9:
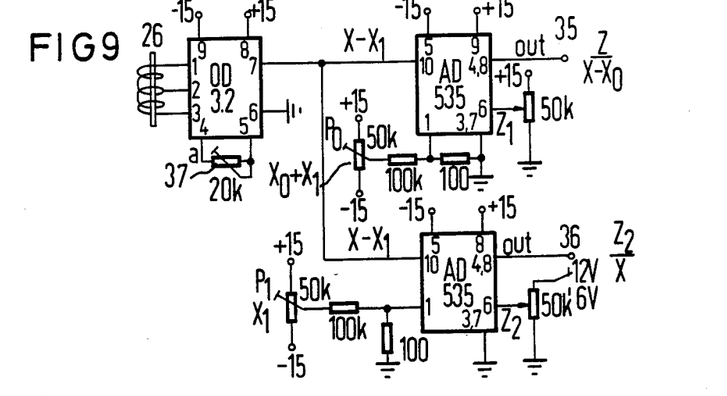
FIG. 9 shows the circuit of an external voltage control for the generation of a continuously variable scale for the position information.

FIG. 9 illustrates a circuit for an external controller 35 for the generation of a continuously variable scale for the local information and for an external control voltage 36 for the displacement of the discriminator window, so that only the desired order of diffraction is detected. The module 27 is connected with the inductive linear encoder 26 via an integrated frequency carrier-amplifier module (Messring Company, Munich 40, Type OD-3.2), which converts the length x into an electric voltage $y = a \cdot (x - x_1)$. The amplification a is adjustable via an external resistance 37, whereas the zero shift $x_1$ is specified by the mechanical construction. This shift $x_1$ must be adapted together with a shift $x_o$ of the detector zero point from the detector center via the potentiometer $P_o$.

The control signal 35 at the input 29 of the TPC must be inversely proportional to the length x. For this purpose, an analog divider-module (e.g. "Analog-Devices" Type AD 535) is employed. This analog divider component possesses the function $y = z/(x - x_o)$, whereby with z, the height of the output voltage 35 can be adjusted. The amplification a is adjusted such that at an overloading is possible at no time, and z is finally adjusted so that in order to satisfy the CPSD-requirement the measured spectral lines remain stationary independent of the movement of the detector PSPC in the multi-channel spectrum.

As in the case of the conventional spectrometers, in the case of an inventive spectrometer the quantum energy, and hence the pulse height, also varies with the Bragg-angle $\theta$. Similarly to the "scanner", the quantum energy is inversely proportional to the distance x between crystal center C and the counter wire center. With a similar function $$y' = z_2/x,$$

which can be generated at a second output 36 of this control module 27, the discriminator window can be so displaced that only the desired order of diffraction is detected.

Decisive for the success of any spectrometer is a high peak/background ratio. While the line width and the beam output or yield enter into the peak height, the background can be unfavorably increased through scattering of the primary beam or of the radiation scattered in air or components of the spectrometer. In a system such as e.g. in the "scanner" of the multi-channel spectrometer MRS 400, wherein only one wavelength at one position is examined, these effects are avoidable in a simple fashion through application of an entry and exit slit in the respective focus of the spectrometer (FIG. 2). The beam path for the wavelength to be analyzed is precisely specified by $\theta$ as well as by $2\theta$ so that the x-ray optical imaging quality of the analyzer crystal 10 (rocking curve) is primarily reflected in the peak output or yield of the spectrometer, but only insignificantly in the resolution.

This is different in an open system, such as operation with a locally resolving detector requires. Here the resolution is dependent alone upon the analyzer crystal 10. Mosaic scatterings must lie below the desired resolution, i.e. below a few 100ths degrees.

Figure 10:
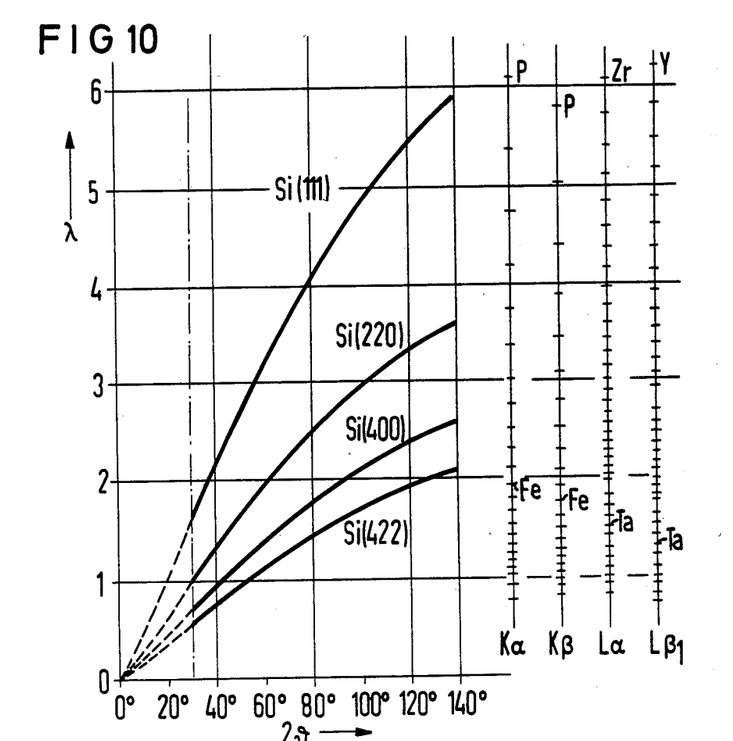
FIG. 10 shows a wavelength scale for differently oriented Si analyzer crystals.

As analyzer crystals 10, e.g. Si analyzer crystals can be employed. This material is available as a semiconductor material in the form of highly perfect disks of a size up to 3 inches (orientation 100, 110, 111). However, it must be noted that the reflectivity is less by nearly one order of magnitude than in the case of the conventionally employed spectrometer crystals. For example, the Si (400-) reflection (d=1.3576A), employed for hard radiation, delivers only a sixth of the intensity of the comparable topaz (303)-reflection. In employing LiF (110) a further doubling of the output or yield as compared with topaz can be expected. If, in the case of Si analyzer crystals, as reflecting lattice planes the interferences (400) and (111) are employed, then these crystals in their first order, together cover the wavelength range of approximately 0.07 nm to 0.6 nm if one assumes that the analyzable angular range of the spectrometer extends from $2\theta = 30°$ to $140°$. Thus, all elements starting from the atomic number 15 (phosphorous) would be detectable with their K or L radiation, respectively (FIG. 10).

Figure 11:
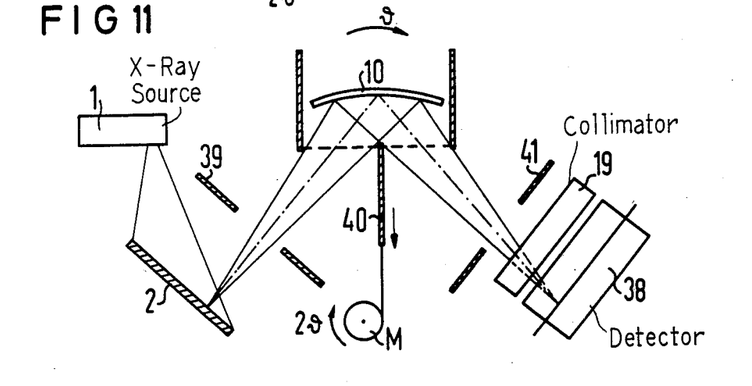
FIG. 11 shows an inventive diaphragm system for the suppression of background radiation.

FIG. 11 illustrates an inventive diaphragm system for the suppression of background radiation. The background due to stray radiation in an open system is difficult to handle. However, the CPSD method permits a rather precise definition of the ray trace, so that through a corresponding diaphragm system, an extensive suppression of the background is possible. The significant constituent part of this diaphragm system is a mobile triple knife-edge diaphragm 40 which is so designed that the crystal 10 in each position is optimally illuminated and that only such radiation reaches the detector 39 which is diffracted or scattered on the crystal 10. A direct look through the three commonly locked-together knife edges is not possible. The movement of the diaphragm 40 is linearly coupled with the $\theta$-$2\theta$ movement, such as indicated in FIG. 11. Additionally, the ray is bounded by an inlet window 39 and outlet window 41. These two windows 39, 41 are applied symmetrically to the crystal axis. They have the task of defining the sample surface to be analyzed and the angular range to be detected by the PSPC 38. The exit window 41 should be selected to be somewhat smaller than, or in the ideal instance equal to, the inlet window 39 and the outlet window 41. A variable exit diaphragm 41, coupled with the $\theta$-$2\theta$ movement, is also conceivable. Finally, there is additionally applied, before the detector 38, a Soller collimator 19 which only allows such rays to pass which run approximately (±1°) parallel to the drawing plane (FIG. 11).

In test measurements, as analyzer crystal 10 for the hard radiation, a Si(400)-crystal was employed. Serving the purpose of excitation of fluorescence radiation a x-ray tube (FK 60-04 W) with a tungsten anode was used which was operated with 40 kV/30 mA. A Cu-sample was intended to convey, in a mean angular range (60°–70°), an impression of the peak/background ratio. With a resolution of approximately 0.2° (full width at half maximum), the $K\alpha_1$-line lies approximately 500 times higher than the background between the $K\alpha$- and $K\beta$- line. The progression of the resolution as a function of the diffraction angle $2\theta$ was examined on the basis of a $V_2A$-steel sample (elements Cr to Ni) in the long wave length range, and on the basis of a sample which contained the elements Ga, As and Zr, in the shortwave range. Already with curved Si-wafers alone, in the Johann-approximation in the long wavelength range (large $2\theta$-angle) an excellent resolution was attained, so that the splitting-up of $CrK\alpha_1$. and $CrK\alpha_2$ (energy difference 9.2 eV) becomes clearly recognizable. The energy resolution here lies at 5.41 keV) below 5 eV.

An inventive x-ray spectrometer will be of significance specifically for the "search for unknown elements", since the method always delivers a complete spectrogram. Through the imaging properties of the employed focusing analyzer crystal, the method operates like a "raster-sequence spectrometer", which continuously sweeps over the sample surface for each element, but which sums up equal wavelengths in equal channels. In utilizing a position-sensitive solid state detector which can be tangentially driven on the focusing circle, it is possible to work with a constant digitizing scale in the case of the incidence location in the PSPC.

Although various minor modifications may be suggested by those versed in the art, it should be understood that I wish to embody within the scope of the patent warranted herein, all such embodiments as reasonably and properly come within the scope of my contribution to the art.

I claim as my invention:

1. A sequential x-ray spectrometer for analyzing x-ray radiation from a sample, comprising: a curved analyzer crystal; position-sensitive detector means for measuring x-ray radiation intensity from the sample via the analyzer crystal; means for displacing the position sensitive detector means during analysis; means for rotating the analyzer crystal so as to scan a surface of the sample; means for rotating the position sensitive detector means during analysis; said curved analyzer crystal being a focusing crystal for focusing the radiation on the detector means; said displacing means displacing the detector means so that a given point of the detector means remains on a focusing circle where the x-ray radiation is focused by the focusing crystal; and the detector means rotating means rotating the detector means through an angle which is twice as large as an angle through which the analyzer crystal is rotated by its rotating means such that during simultaneous displacement of the detector means on the focusing circle, the given point of the detector means remains at the focus.

2. A sequential x-ray spectrometer according to claim 1 wherein the analyzer crystal is rotatable.

3. A sequential x-ray spectrometer according to claim 1 wherein the position-sensitive detector means is a position-sensitive proportional counter tube (PSPC).

4. A sequential x-ray spectrometer according to claim 3 wherein means are provided for moving the position-sensitive proportional counter tube (PSPC) in an uninterrupted motion.

5. A sequential x-ray spectrometer according to claim 1 wherein means are provided for limiting the detected radiation beam to substantially direct rays passing to the detector means from the analyzer crystal.

6. A sequential x-ray spectrometer according to claim 1 wherein movement of the triple knife edge diaphragm is coupled to movements of the analyzer crystal and of the detector means.

7. A sequential x-ray spectrometer according to claim 5 wherein a variable exit diaphragm means is positioned adjacent the detector means for changing a coverable angular range of incident radiation on the detector means.

8. A sequential x-ray spectrometer according to claim 5 wherein a Soller collimator is provided between an exit diaphragm and the detector means.

9. A sequential x-ray spectrometer according to claim 5 wherein a triple-knife edge diaphragm means is positioned adjacent the analyzer crystal and which moves such that the analyzer crystal is optimally illuminated in every position, said diaphragm means providing that only such radiation directly proceeding from the analyzer crystal to the detector means reaches the detector means in every position of the analyzer crystal and of the detector means.

10. A sequential x-ray spectrometer according to claim 1 wherein means are provided for counting x-rays of equal wavelength into equal channels of an electronic analysis means of the spectrometer such that a channel address for a given diffraction angle of an x-ray quantum results through addition of the addresses for an angular position of the position-sensitive detector means and for incidence location of the x-ray quantum in the detector means.

11. A sequential x-ray spectrometer according to claim 10 wherein means are provided for linearly digitizing and in the same scale the addresses to be added.

12. A sequential x-ray spectrometer according to claim 8 wherein means are provided for connecting an angular scale for the incidence location in the detector means in correspondence with the distance of the analyzer crystal detector means from the detector means.

13. A sequential x-ray spectrometer according to claim 1 wherein the means for moving includes a linear guidance means.

14. A sequential x-ray spectrometer according to claim 13 wherein at least one stepping motor drive is provided.

15. A sequential x-ray spectrometer according to claim 14 wherein an electronic coupling of two stepping motor drives is provided.

16. A sequential x-ray spectrometer according to claim 14 wherein a mechanical coupling of two rotational movements is provided.

17. A sequential x-ray spectrometer for analyzing x-ray radiation from a sample, comprising: a curved analyzer crystal which comprises a focusing crystal; means for pivoting the analyzer crystal about an axis thereof during analysis so as to scan a surface of the sample; position-sensitive detector means for measuring x-ray radiation intensity from the analyzer crystal;

means for displacing the position-sensitive detector means during analysis; means for rotating the detector means; and said pivoting means, rotating means, and displacing means being coordinated such that an angular rotation of the detector means is twice as large as a pivoting angle of the analyzing crystal and wherein the detector means is simultaneously displaced on a focusing circle of the spectrometer so that a center of the detector means remains in focus and such that the detector means faces the incoming x-ray radiation from the analyzer crystal.

18. A spectrometer according to claim 17 wherein the position-sensitive detector means is rotated and displaced in order to coordinate its movement with the rotation of the analyzer crystal.

19. A spectrometer according to claim 17 wherein the detector means is aligned perpendicularly relative to incoming x-ray radiation from a center of the analyzer crystal.

* * * * *